US012690533B2

(12) United States Patent (10) Patent No.: US 12,690,533 B2
Koorevaar et al. (45) Date of Patent: Jul. 28, 2026

(54) **CHLOROSIS RESISTANT CYTOPLASMIC MALE STERILE *BRASSICA* PLANTS**

(71) Applicant: Enza Zaden Beheer B.V., Enkhuizen (NL)

(72) Inventors: Gerard Nijs Koorevaar, Enkhuizen (NL); Roy Briga, Enkhuizen (NL); Ilja Roobeek, Enkhuizen (NL); Brenda Johanna Maria De Lange, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 252 days.

(21) Appl. No.: 18/265,914

(22) PCT Filed: Dec. 10, 2020

(86) PCT No.: PCT/EP2020/085628
§ 371 (c)(1),
(2) Date: Jun. 7, 2023

(87) PCT Pub. No.: WO2022/122164
PCT Pub. Date: Jun. 16, 2022

(65) Prior Publication Data
US 2024/0032496 A1 Feb. 1, 2024

(51) Int. Cl.
*A01H 6/20* (2018.01)
*A01H 1/00* (2006.01)
*A01H 1/02* (2006.01)
*A01H 5/12* (2018.01)

(52) U.S. Cl.
CPC ............. *A01H 6/204* (2018.05); *A01H 1/023* (2021.01); *A01H 1/1225* (2021.01); *A01H 5/12* (2013.01)

(58) Field of Classification Search
CPC ....................................................... A01H 6/204
USPC .......................................................... 800/260
See application file for complete search history.

(56) References Cited

U.S. PATENT DOCUMENTS 5,254,802 A 10/1993 Hoekstra et al.

FOREIGN PATENT DOCUMENTS

| JP | H07-31307 A | 2/1995 | |
| WO | WO-97/09873 A1 | 3/1997 | |
| WO | WO-01/54487 A1 | 8/2001 | |
| WO | WO-2010/042974 A1 | 4/2010 | |
| WO | WO-2020213728 A1 * | 10/2020 | ........... C12Q 1/6895 |

OTHER PUBLICATIONS

Kwon et al. Genbank Accession No. AC 189190 (Year: 2006).*
Huh et al. Genbank Accession No. FX726839 (Year: 2014).*
Dong et al., "Ogura-CMS in Chinese cabbage (*Brassica rapa* ssp. *pekinensis*) causes delayed expression of many nuclear genes," Plant Science 199-200: pp. 7-17 (2013).
Hou et al., "Creation of a New Germplasm of CMS Non-Heading Chinese Cabbage," Proc. XXVI IHC—Advances in Vegetable Breeding, Acta Hort. 637: pp. 75-81 (2004).
International Search Report and Written Opinion for International Application No. PCT/EP2020/085628, mailed Aug. 31, 2021.

* cited by examiner

*Primary Examiner* — Li Zheng
(74) *Attorney, Agent, or Firm* — Foley Hoag LLP; Brendan T. Jones

(57) ABSTRACT

The present invention relates to a chlorosis resistant cytoplasmic male sterile (CMS) *Brassica rapa* plant and methods of producing the chlorosis resistant CMS *Brassica rapa* plant. The present invention further relates to progeny, a descendent plant, and/or seed and/or plant part of the chlorosis resistant CMS *Brassica rapa* plant.

5 Claims, 3 Drawing Sheets

Figure 1:
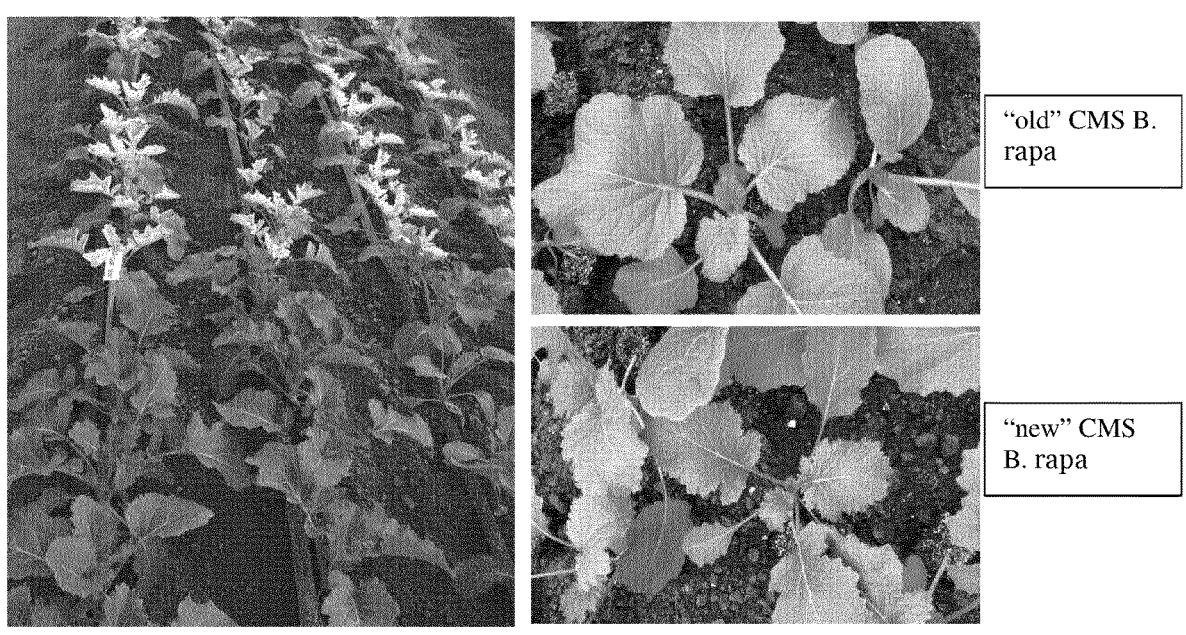

Specification includes a Sequence Listing.

"old" CMS *B. rapa*          "new" CMS *B. rapa*          Wild type *B. rapa*

```
                             SEQUENCE LISTING

<160>  NUMBER OF SEQ ID NOS: 23

<210>  SEQ ID NO 1
<211>  LENGTH: 79
<212>  TYPE: DNA
<213>  ORGANISM: Artificial Sequence
<220>  FEATURE:
<223>  OTHER INFORMATION: Cp Rapa 1

<400>  SEQUENCE: 1 gaaatatgac caactgtggt tcgaatatat ataaaaaaag tttgtttttt tacacttctt        60
actatcagat agtgtgcat                                                     79

<210>  SEQ ID NO 2
<211>  LENGTH: 79
<212>  TYPE: DNA
<213>  ORGANISM: Artificial Sequence
<220>  FEATURE:
<223>  OTHER INFORMATION: Cp Oleracea 1

<400>  SEQUENCE: 2 gaaatatgac caactgtggt tcgaatatat atacaaaaag tttgtttttt tacacttctt        60
actatcagat agtgtgcat                                                     79

<210>  SEQ ID NO 3
<211>  LENGTH: 101
<212>  TYPE: DNA
<213>  ORGANISM: Artificial Sequence
<220>  FEATURE:
<223>  OTHER INFORMATION: Cp Rapa 2

<400>  SEQUENCE: 3 ctcgaacaag taatcgaaaa gattctggag catcttctgg tttaggtatt gctcctccaa        60
tgatagtggt accaagtact tcttggcgag ctctaatatg a                          101

<210>  SEQ ID NO 4
<211>  LENGTH: 101
<212>  TYPE: DNA
<213>  ORGANISM: Artificial Sequence
<220>  FEATURE:
<223>  OTHER INFORMATION: Cp Oleracea 2
```

-continued

<400> SEQUENCE: 4
ctcgaacaag taatcgaaaa gattctggag catcttctgg tttaggtatt gttcctccaa      60
tgatagtggt accaagtact tcttggcgag ctctaatatg a                        101

<210> SEQ ID NO 5
<211> LENGTH: 117
<212> TYPE: DNA
<213> ORGANISM: Artificial Sequence
<220> FEATURE:
<223> OTHER INFORMATION: Cp Rapa 3

<400> SEQUENCE: 5
aaggattcat aagtagttgt taacggagtt gaagttacca aattctgagg agtcggtatc      60
aatttatgcc taattgctcc gcctatagtt cccttaacta cattttctaa acgagcc        117

<210> SEQ ID NO 6
<211> LENGTH: 117
<212> TYPE: DNA
<213> ORGANISM: Artificial Sequence
<220> FEATURE:
<223> OTHER INFORMATION: Cp Oleracea 3

<400> SEQUENCE: 6
aaggattcat aagtagttgt taacggagtt gaagttacca aattctgagg agtaggtatc      60
aatttatgcc taattgctcc gcctatagtt cccttaacta cattttctaa acgagcc        117

<210> SEQ ID NO 7
<211> LENGTH: 107
<212> TYPE: DNA
<213> ORGANISM: Artificial Sequence
<220> FEATURE:
<223> OTHER INFORMATION: N Rapa 1

<400> SEQUENCE: 7
tcggtcaagg actcggatac atcgatgctg gagcacaaaa agaagcagaa ggaagagaaa      60
acagcgatgg aggaagagat ggagaagctg agaagagatc aggcgga                   107

<210> SEQ ID NO 8
<211> LENGTH: 107
<212> TYPE: DNA
<213> ORGANISM: Artificial Sequence
<220> FEATURE:
<223> OTHER INFORMATION: N Oleracea 1

<400> SEQUENCE: 8
tcggtcaagg actcggatac atcgatgctg gagcataaga agaagcagaa ggaagagaaa      60
acagcgatgg aggaagagat ggagaagctg agaagagatc aggcgga                   107

<210> SEQ ID NO 9
<211> LENGTH: 122
<212> TYPE: DNA
<213> ORGANISM: Artificial Sequence
<220> FEATURE:
<223> OTHER INFORMATION: N Rapa 2

<400> SEQUENCE: 9
ctgtgcctcg gaaaggtgag tatcttgtgt tggaagttta ttttctttgt ctctcagtga      60
tctcatgcat acacaaactt ttgtgcagcc tgcggatata tacctgattg atgagccaag     120
tg                                                                    122

-continued

```
<210> SEQ ID NO 10
<211> LENGTH: 122
<212> TYPE: DNA
<213> ORGANISM: Artificial Sequence
<220> FEATURE:
<223> OTHER INFORMATION: N Oleracea 2

<400> SEQUENCE: 10
ctgtgcctcg gaaaggtgag tatcttgtgt tggaagtttg ttttctttgt ctctcagtga     60
tctcatgcat acacaaactt ttgtgcagcc tgcggatata tacctgattg atgagccaag    120
tg                                                                    122

<210> SEQ ID NO 11
<211> LENGTH: 58
<212> TYPE: DNA
<213> ORGANISM: Artificial Sequence
<220> FEATURE:
<223> OTHER INFORMATION: Mt Ogura

<400> SEQUENCE: 11
aagaagcaaa atctcattca atttgaaata gaagagatct ctatgccccc tgttcttg      58

<210> SEQ ID NO 12
<211> LENGTH: 20
<212> TYPE: DNA
<213> ORGANISM: Artificial Sequence
<220> FEATURE:
<223> OTHER INFORMATION: Mt Rapa 1 Fw

<400> SEQUENCE: 12
tcccctctgt ccctatgttg                                                 20

<210> SEQ ID NO 13
<211> LENGTH: 20
<212> TYPE: DNA
<213> ORGANISM: Artificial Sequence
<220> FEATURE:
<223> OTHER INFORMATION: Mt Rapa 1 Rev

<400> SEQUENCE: 13
gaggtgttgc ctatccaggt                                                 20

<210> SEQ ID NO 14
<211> LENGTH: 21
<212> TYPE: DNA
<213> ORGANISM: Artificial Sequence
<220> FEATURE:
<223> OTHER INFORMATION: Mt Rapa 2 Fw

<400> SEQUENCE: 14
ttcgttcgtt cacttcgttc t                                               21

<210> SEQ ID NO 15
<211> LENGTH: 21
<212> TYPE: DNA
<213> ORGANISM: Artificial Sequence
<220> FEATURE:
<223> OTHER INFORMATION: Mt Rapa 2 Rev

<400> SEQUENCE: 15
aggcctttcc ttaagcttcc t                                               21

<210> SEQ ID NO 16
<211> LENGTH: 21
<212> TYPE: DNA
```

-continued

```
<213> ORGANISM: Artificial Sequence
<220> FEATURE:
<223> OTHER INFORMATION: Mt Rapa 3 Fw

<400> SEQUENCE: 16
ggaaggatcg aaccatagga a                                                21

<210> SEQ ID NO 17
<211> LENGTH: 22
<212> TYPE: DNA
<213> ORGANISM: Artificial Sequence
<220> FEATURE:
<223> OTHER INFORMATION: Mt Rapa 3 Rev

<400> SEQUENCE: 17
ttgatgagcc tttacgagtt ga                                               22

<210> SEQ ID NO 18
<211> LENGTH: 21
<212> TYPE: DNA
<213> ORGANISM: Artificial Sequence
<220> FEATURE:
<223> OTHER INFORMATION: Mt Oleracea 1 Fw

<400> SEQUENCE: 18
cgaaaacctt ctgttctgtg g                                                21

<210> SEQ ID NO 19
<211> LENGTH: 20
<212> TYPE: DNA
<213> ORGANISM: Artificial Sequence
<220> FEATURE:
<223> OTHER INFORMATION: Mt Oleracea 1 Rev

<400> SEQUENCE: 19
cggagcgtaa ccactttctt                                                  20

<210> SEQ ID NO 20
<211> LENGTH: 20
<212> TYPE: DNA
<213> ORGANISM: Artificial Sequence
<220> FEATURE:
<223> OTHER INFORMATION: Mt Oleracea 2 Fw

<400> SEQUENCE: 20
attccccacc caaccaatac                                                  20

<210> SEQ ID NO 21
<211> LENGTH: 21
<212> TYPE: DNA
<213> ORGANISM: Artificial Sequence
<220> FEATURE:
<223> OTHER INFORMATION: Mt Oleracea 2 Rev

<400> SEQUENCE: 21
aagagcagct ttctccgttc t                                                21

<210> SEQ ID NO 22
<211> LENGTH: 20
<212> TYPE: DNA
<213> ORGANISM: Artificial Sequence
<220> FEATURE:
<223> OTHER INFORMATION: Mt Oleracea 3 Fw

<400> SEQUENCE: 22
ttgctgtatc ggaaagtcca                                                  20
```

-continued

```
<210> SEQ ID NO 23
<211> LENGTH: 20
<212> TYPE: DNA
<213> ORGANISM: Artificial Sequence
<220> FEATURE:
<223> OTHER INFORMATION: Mt Oleracea 3 Rev

<400> SEQUENCE: 23
gcatgtcgta agcgagtcaa                                                                    20
```

CHLOROSIS RESISTANT CYTOPLASMIC MALE STERILE *BRASSICA* PLANTS

RELATED APPLICATIONS

This application is a U.S. National Phase of International Patent Application No. PCT/EP2020/085628, filed Dec. 10, 2020, which is hereby incorporated by reference in its entirety.

The present invention relates to a chlorosis resistant cytoplasmic male sterile (CMS) *Brassica rapa* plant and methods of producing the chlorosis resistant CMS *B. rapa* plant. The present invention further relates to progeny, descendent plant, seed or plant part of the chlorosis resistant CMS *B. rapa* plant.

Cytoplasmic male sterility (CMS) is total or partial male sterility in plants as the result of specific nuclear and mitochondrial interactions. Male sterility is the failure of plants to produce functional anthers, pollen, or male gametes. CMS is under extranuclear genetic control, i.e. under control of the mitochondrial or plastid genomes and is a maternally inherited trait encoded by a gene in the mitochondria and/or plastids. CMS systems are widely exploited in crop plants for hybrid breeding due to the convenience of controlling sterility expression by manipulating the gene-cytoplasm combinations. Male-sterile cytoplasms can be restored to fertility by certain nuclear Rf genes. Several types of CMS can be distinguished on the basis of the specific nuclear genes that restore the failure of plants to produce functional anthers, pollen, or male gametes. Incorporation of CMS systems for male sterility evades the need for emasculation in cross-pollinated species, thus encouraging cross breeding producing only hybrid seeds under natural conditions.

One particular CMS system was developed for use in *Brassica* plants, especially in *Brassica oleracea, B. napus, B. juncea* wherein only the cytoplasm (i.e. mitochondria) of Ogura (Japanese radish) was transferred to these *Brassica* plants. Gene expression changes by dysfunctional mitochondria in Ogura CMS results in pollen development defects, but little is known about gene expression effects in vegetative tissues of the plant. Mitochondrial influence on the nuclear gene expression is referred to as mitochondrial retrograde regulation and it occurs in CMS lines via CMS-inducing genes. In addition, chloroplastic retrograde signalling changes both nuclear and mitochondrial gene expression, and little is known about the regulation of chloroplast genes and nuclear genes for chloroplast proteins by mitochondrial retrograde signalling. However, with the introduction of the CMS also several undesirable characteristics were transferred to the CMS crop which are likely the consequence of incongruity between the *Brassica* nucleus, chloroplast and Ogura mitochondria.

A drawback of the production of CMS hybrids in *Brassica*'s is that introgression with Ogura cytoplasm into *Brassica* plants results in chlorosis of the leaves at low temperatures, i.e. discoloration or yellowing of the plant tissues as compared to their fertile analogs. Ogura mitochondria with accompanying *B. oleracea* chloroplasts in *B. rapa* cause chlorosis in leaves in colder growing conditions. Recent studies indicate that reduction in thylakoid proteins and chlorophylls lead to reduction in photosynthetic effect and chlorosis of Ogura-CMS at low temperatures. For example, a *B. napus* plant that was produced by chloroplast fusion and contained the Ogura CMS, showed chlorosis at low temperature (below 15° C.). In Ogura-CMS Chinese cabbage (*B. rapa* spp *pekinensis*), showed, next to chlorotic effect, a reduced plant height, delayed flowering, and shorter filaments.

Several attempts have been made to overcome such adverse affect due to the CMS including the chlorosis. Somatic fusion, i.e. chloroplast fusions were attempted by which two distinct species of *Brassica* plants are fused together to form a new hybrid plant with the characteristics of both. However this approach leads to *Brassica* lines having severe floral deformities and poor seed setting and chlorosis remained an issue. Others trying to optimize the CMS Ogura-based system observed the production of smaller, less compact, less vigorous, low quality and still chlorotic plant parts and fruits. With the change in cytoplasm genome through addition of chloroplasts of radish with chloroplasts of *B. oleracea*, some of the negative traits were corrected, however especially chlorosis remained an issue. This because over time, the *B. oleracea* chloroplasts that are present in the hybrid cells will be outcompeted by the chloroplasts of radish and the chlorosis will remain an issue after several generations of growth. Chloroplasts accompanying Ogura CMS were reported to be preferred during meiosis in mixed chloroplast cytoplasm outnumbering alternative chloroplasts, which resulted in returning of the yellowing phenotype, i.e. chlorosis in later backcross generations. Retrograde signalling or organelle interaction is regulated at the protein level and is unique to the *Brassica* species used in breeding. Therefore, it seems that finding the optimal combination between nucleus and organelles is a prerequisite for CMS-based breeding.

At present there is no CMS system for hybrid breeding available that overcomes the adverse effects on the plants and fruits, especially over longer periods of time (i.e. several generations of growing and cultivation). Several types of CMS systems are well known and being used in hybrid production, including Polima (pol), hau, nap, and Ogura (ogu) CMS, but all exhibited negative effects on the hybrid plants. The pol CMS is temperature sensitive and therefore limited in its use for hybrid production. Furthermore, the main disadvantage of the pol CMS system is that male sterility is sensitive to the environment in different nuclear backgrounds, leading to its breakdown, and thus (in part) restoration of fertility during the process of hybrid seed production. The negative effect of Ogura cytoplasm on the plants and crops results in commercially less interesting hybrid seed production using such CMS lines. Furthermore, *Brassica* plants that show chlorosis are not acceptable for commercial sale. However, despite its limitations, the Ogura-CMS system remains the best option (i.e. heaving the least adverse effects) for the production of *Brassica* hybrid seeds.

Considering the above, there is a need in the art for a CMS *Brassica* plant that is able to produce hybrid seeds and to resist the negative effects on agronomic performance due to the CMS system, including chlorotic effects at exposure to low temperatures over an extended period of growth and cultivation, a reduced plant height, delayed flowering, and shorter filaments. In addition, there is a need in the art for a method for providing such CMS *Brassica* plants.

It is an object of the present invention, amongst other objects, to address the above need in the art. The object of present invention, amongst other objects, is met by the present invention as outlined in the appended claims.

Specifically, the above object, amongst other objects, is met, according to a first aspect, by the present invention by a chlorosis resistant cytoplasmic male sterile (CMS) *Brassica rapa* plant, wherein:

substantially 100% of the chloroplasts in the plant are *Brassica rapa* (*B. rapa*) chloroplasts, said *Brassica rapa* chloroplasts are identifiable by one or more sequences selected from the group consisting of SEQ ID No. 1, SEQ ID No. 3 and SEQ ID No. 5;

the nuclear genome of the plant is a *Brassica rapa* nuclear genome identifiable by SEQ ID No. 7 and/or SEQ ID No. 9; and the plant does not comprise *Brassica oleracea* (*B. oleracea*) chloroplasts identifiable by one or more sequences selected from the group consisting of SEQ ID No. 2, SEQ ID No. 4, and SEQ ID No. 6.

The cells of the plant comprise chloroplasts and a nucleus that originate from *B. rapa* only, wherein the chloroplasts are associated with SEQ ID No. 1, SEQ ID No. 3 and/or SEQ ID No. 5, or having at least 95%, preferably at least 96%, more preferably at least 97%, even more preferably at least 98%, most preferably at least 99% sequence identity with said sequences. In the CMS plants of present invention mitochondria of a source providing CMS (e.g. Ogura) are combined with *B. rapa* chloroplasts and a *B. rapa* nucleus by cell fusion. SEQ ID No. 1, SEQ ID No. 3 and/or SEQ ID No. 5 identify the origin of the chloroplast organelle being from *B. rapa*. The nucleus is associated with SEQ ID No. 7 or 9, or having at least 98%, preferably at least 99%, more preferably 100% sequence identity with said sequences and identifies the origin of the nucleus being from *B. rapa*. The nucleus of the plant of present invention only comprises the nucleus of *B. rapa* and may further be analysed for the absence of *B. oleracea* sequences, i.e. by the absence of SEQ ID No. 8 or SEQ ID No. 10. Further marker analysis may be performed on the organelles, i.e. mitochondria, nucleus to confirm that the CMS *B. rapa* plants comprised 100% of *B. rapa* chloroplasts, nucleus and comprise mitochondria of for example Ogura. The *B. rapa* plants according to present invention do not show chlorosis and are suitable for commercial sale. The CMS *B. rapa* plant of present invention is similar in size and shape, showing no adverse affects of the on plant growth and development. Also after further backcrosses in F1 no chlorosis and adverse effects on plant growth and plant development was observed in the CMS *B. rapa* plants of present invention.

The CMS plant of present invention does not suffer of the consequence of the incompatibility between the *Brassica* nucleus, chloroplast and Ogura mitochondria, since both the nucleus and chloroplast both fully originate from *B. rapa*. It is thought that there is no reduction in thylakoid proteins and chlorophylls that will lead to a reduction in photosynthetic efficiency and chlorosis at low temperatures, i.e. no yellowing of the plant parts. There is also no increase in chlorosis after long term breeding, as has been observed in previous CMS *Brassica* species that have tried to overcome the chlorosis effect. Therefore, a stable chlorosis resistant CMS *B. rapa* is provided herewith, that shows normal plant growth and no negative effects on agronomic performance. As indicated earlier, regular protoplast fusion in the art is between a *B. rapa* and a *B. oleracea* Ogura donor (providing the CMS trait), i.e. using *B. oleracea* chloroplast and Ogura mitochondrion as donor. This however this leads to *Brassica* lines showing chlorosis. Surprisingly, the *B. rapa* of present invention is obtained by protoplast fusion of a selected CMS *B. rapa* that shows chlorosis (i.e. is not chlorosis resistant) with a wild type *B. rapa* (non CMS) to provide a new CMS *B. rapa* plant that is chlorosis resistant and does not suffer from negative effect on plant vigour or seed setting as was shown for other known CMS Ogura-based systems in *Brassica*.

According to a preferred embodiment, the present invention relates to the chlorosis resistant CMS *B. rapa* plant, wherein the plant is obtainable by a method comprising the steps of:

a) protoplast fusion of protoplasts of a fertile *Brassica rapa* plant as the protoplast donor with protoplasts of CMS *Brassica rapa* plant comprising chloroplasts of another diploid species of *Brassica*, preferably *Brassica oleracea*, as cytoplasm donor;

b) selecting protoplast fusion products wherein:

substantially 100% of the chloroplasts in the plant are *Brassica rapa* chloroplasts identifiable by one or more sequences selected from the group consisting of SEQ ID No. 1, SEQ ID No. 3 and SEQ ID No. 5;

the nuclear genome of the plant is a *Brassica rapa* nuclear genome identifiable by SEQ ID No. 7 and/or SEQ ID No. 9; and the plant does not comprise *Brassica oleracea* chloroplasts identifiable by one or more sequences selected from the group consisting of SEQ ID No. 2, SEQ ID No. 4, and SEQ ID No. 6.

According to a preferred embodiment of the present invention the present plants detailed above are not plants exclusively obtained by means of an essentially biological process. The plant does not comprise chloroplasts that originate from *B. oleracea*.

According to another preferred embodiment, the present invention relates to the chlorosis resistant CMS *B. rapa* plant wherein the plant comprises a mitochondrial genome of *R. sativus* (Radish, also referred to as Ogura or Orgura-CMS), *B. oxyrrhina* (wild mustard), *D. muralis* (annual wall-rocket), *M. arvensis* (wild mint), or *E. lyratus* (dragonfly), preferably *R. sativus*. The Ogura-CMS system is the preferred system for providing the mitochondrial genome, i.e. sterility.

According to another preferred embodiment, the present invention relates to the chlorosis resistant CMS *B. rapa* plant, wherein:

substantially 100% of the mitochondria are *R. sativus* mitochondria identifiable SEQ ID No. 11;

the plant does not comprise *Brassica oleracea* and *Brassica rapa* mitochondria.

The cells of the plant comprise a mitochondrial genome associated with SEQ ID No. 11, or having at least 95%, preferably at least 96%, more preferably at least 97%, even more preferably at least 98%, most preferably at least 99% sequence identity with said sequence and identifies the origin of the mitochondrial genome being from *R. sativus* (Ogura). SEQ ID No. 12 to SEQ ID No. 23 are primer sequences that may be used to determine if the mitochondria comprise *B. rapa* or *B. oleracea* mitochondrial sequences.

According to a preferred embodiment, the present invention relates to the chlorosis resistant CMS *B. rapa* plant, wherein the *B. rapa* plant is selected from the group of *B. rapa* subspecies consisting of *rapa, pekinensis, glabra, chinensis, rapifera, oleifera, parachinensis, perviridis, Brassica narinosa, trilocularis, mizuna*, preferably *rapa* or *pekenensis. Brassica rapa* is a plant consisting of various widely cultivated species including the turnip (*Brassica rapa* subsp. *rapa*); napa cabbage (*Brassica rapa* subsp. *pekinensis*), bomdong (*Brassica rapa* var. *glabra*), bok Choy (*Brassica rapa* subsp. *chinensis*), and Rapini (*Brassica rapa* var. *rapifera*), an oilseed which has many common names, including turnip rape, field mustard (*Brassica rapa* subsp. *oleifera*), bird rape, and keblock. Choy sum (*Brassica rapa* subsp. *parachinensis*), Komatsuna (*Brassica rapa* subsp. *perviridis*), Tatsoi (*Brassica rapa* subsp. *narinosa*), Yellow Sarson (*Brassica rapa* subsp. *trilocularis*) and *Mizuna* (*Brassica rapa* subsp. *niposinica*).

According to yet another preferred embodiment, the present invention relates to the chlorosis resistant CMS *B. rapa* plant, wherein:

substantially 100% of the chloroplast are chloroplasts derived from NCIMB Accession Number 43622;

substantially 100% of the mitochondria are mitochondria derived from NCIMB Accession Number 43622.

Representative seeds have been deposited under NCIMB Accession Number 43622 on 26 May 2020 at NCIMB Ltd. Ferguson Building, Craibstone Estate, Bucksburn, Aberdeen, AB21 9YA Scotland.

The present invention, according to a further aspect, relates to progeny or a descendent plant, a seed or plant part of the chlorosis resistant CMS *B. rapa* plant of present invention.

The present invention, according to a further aspect, relates to a hybrid *Brassica* plant produced using the chlorosis resistant CMS *B. rapa* plant of present invention. The present invention, according to a further aspect, relates to a method for providing a chlorosis resistant CMS *Brassica rapa* plant, comprising the steps of;

a) protoplast fusion of protoplasts of a fertile *Brassica rapa* plant as the chloroplast donor with protoplasts of CMS *Brassica rapa* plant comprising chloroplasts of another diploid species of *Brassica*, preferably *Brassica oleracea*, as cytoplasm donor;

b) selecting protoplast fusion products wherein:

substantially 100% of the chloroplasts in the plant are *Brassica rapa* chloroplasts identifiable by one or more sequences selected from the group consisting of SEQ ID No. 1, SEQ ID No. 3 and SEQ ID No. 5;

the nuclear genome of the plant is a *Brassica rapa* nuclear genome identifiable by SEQ ID No. 7 and/or SEQ ID No. 9; and the plant does not comprise *Brassica oleracea* chloroplasts identifiable by one or more sequences selected from the group consisting of SEQ ID No. 2, SEQ ID No. 4, and SEQ ID No. 6;

optionally, crossing at least one time the selected chlorosis resistant CMS *Brassica rapa* plant with a wild type *Brassica rapa* plant and selecting a chlorosis resistant CMS *Brassica rapa* plant. The method of present invention uses in step a) the CMS *B. rapa* that is not chlorosis resistant (i.e. shows chlorosis) and a wild type *B. rapa* (non CMS) to perform a protoplast fusion and to subsequently select (step c) and provide a new CMS *B. rapa* plant that is chlorosis resistant. The chlorosis resistant CMS *B. rapa* plant of present invention comprises mitochondria of Ogura only, and chloroplasts of *B. rapa* only and a *B. rapa* nucleus. Furthermore, this plant does not suffer from negative effect on plant vigour or seed setting as was shown for other known CMS Ogura-based systems in *Brassica*.

According to yet another preferred embodiment, the present invention relates to the method, wherein the mitochondrial genome of the plant is derived from *R. sativus* (Radish), *B. oxyrrhina* (wild mustard), *D. muralis* (annual wallrocket), *M. arvensis* (wild mint), *E. lyratus* (dragonfly), preferably *R. sativus*.

According to a preferred embodiment, the present invention relates to the method, wherein selecting is further performed by selecting the plants comprising a mitochondrial genome associated with SEQ ID No. 11, and wherein the plant does not comprise *B. oleracea* or *B. rapa* mitochondrial sequences. The cells of the plant comprise a mitochondrial genome associated with SEQ ID No. 11, or having at least 95%, preferably at least 96%, more preferably at least 97%, even more preferably at least 98%, most preferably at least 99% sequence identity with said sequence and identifies the origin of the mitochondrial genome being from *R. sativus* (Ogura). SEQ ID No. 12 to SEQ ID No. 23 are primer sequences that may be used to determine if the mitochondria comprise *B. rapa* or *B. oleracea* mitochondrial sequences.

According to yet another preferred embodiment, the present invention relates to the method, wherein the *B. rapa* plant is selected from the group of *B. rapa* subspecies consisting of *rapa, pekinensis, glabra, chinensis, rapifera, oleifera, parachinensis, perviridis, Brassica narinosa, trilocularis*, preferably *rapa* or *pekenensis*.

The present invention will be further detailed in the following examples and figures wherein:

FIG. 1: shows CMS *B. rapa* plants in a non heated glass house for winter cultivation (temperatures between 5 to 12° C.). The upper 3 to 4 rows of plants comprise the prior art "old" CMS *B. rapa* plant and show clear yellowing of the leaves, i.e. chlorosis. The lower rows of plants are CMS *B. rapa* plants according to present invention that is chlorosis resistant, having a *B. rapa* nucleus, Ogura mitochondria and *B. rapa* chloroplast.

Figure 2:
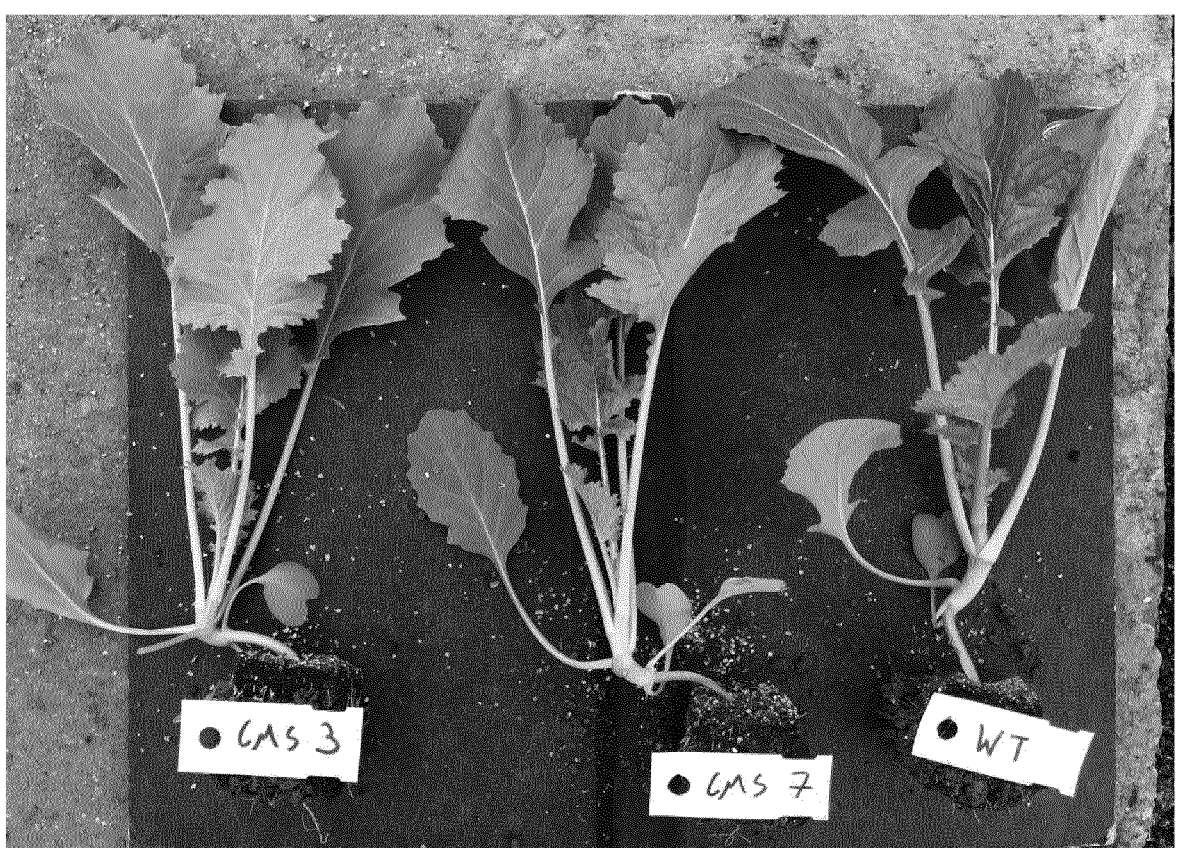
Figure 2:
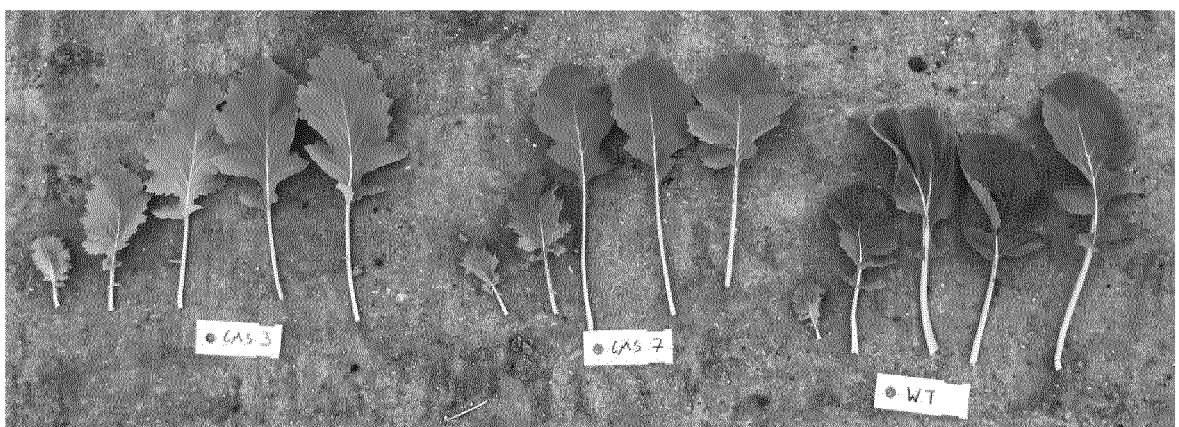

FIG. 2: shows leaves of a prior art CMS *B. rapa* plant (left, CMS3), a CMS *B. rapa* plant according to present invention having a *B. rapa* nucleus, Ogura mitochondria and *B. rapa* chloroplast that is chlorosis resistant (middle, CMS7), and a wild type *B. rapa* plant (right, WT). The CMS *B. rapa* plant on the left is showing first signs of chlorosis after 3 to 4 weeks of cultivation in a non heated glass house at temperatures between 5 to 12° C. Chlorosis is especially visible from the stem of the leaves, gradually moving towards the leave. No chlorosis was visible on the CMS *B. rapa* plant (middle) of present invention during these 3 to 4 weeks under identical conditions, similar to the WT *B. rapa*. Furthermore, the CMS plant of present invention shows regular growth, comparable to the "old" CMS and wild type *B. rapa*.

Figure 3:
Figure 3:

FIG. 3: shows the flowers of a chlorosis resistant CMS *B. rapa* plant of present invention (upper picture) and a wild type male fertile *B. rapa* plant (lower picture). The CMS plant of present invention shows the male sterility throughout the whole plant. Pollen are clearly visible on the wild type male fertile *B. rapa* plant having fully developed anthers that carry pollen grains, whereas the CMS *B. rapa* plant of present invention shows undeveloped anthers and the anthers are carrying no pollen at all.

EXAMPLES

Generation of Chlorosis Resistant *B. rapa* Ogura CMS of Present Invention

A *B. rapa* var. *cymosa* (Cime di *Rapa*) fertile line and an Ogura CMS *B. rapa* (Cime di *Rapa*) line with *Brassica oleracea* chloroplasts were grown for 14 days before protoplast fusion. The leaves of a *Brassica rapa* var. *cymosa* (Cime di *Rapa*) fertile line grown for 14 days before protoplast fusion is used and an Ogura CMS *Brassica rapa* (Cime di *Rapa*) line with *Brassica oleracea* chloroplasts grown for 7 days in the dark for etiolated hypocotyl protoplasts are used. Then the leaves of the *B. rapa* fertile line seedling and the etiolated hypocotyl of the Ogura CMS *Brassica rapa* (Cime di *Rapa*) line were used for protoplast fusion known in the art, such as Pelletier et al.1983, Molecular and General Genetics MGG 191:244-250.

Briefly, leaf and hypocotyl material is cut into small pieces and placed in a petri dish containing a layer (~12 ml) of plasmolysing solution and subsequently wrapped in aluminum foil and stored in a laminar flow cabinet for at least one hour. Next, the plasmolysing solution is replaced by equal amounts of enzyme solution and incubated overnight in aluminum foil at 25° C., wherein the petri dishes comprising the hypocotyl protoplasts is placed on a shaker at 30 rpm and an amplitude of 15 mm Next day, the obtained suspension samples are filtered over a Teflon filter holder with two nylon filters of 110 μm and 53 μm respectively. The filters are re-rinsed with 8-9 ml of CPW16. Then, the suspensions are centrifuged at 110×g for 5 minutes providing visible protoplast bodies. The protoplasts samples are transferred to a fresh centrifuge tube via a Pasteur pipette. Then, approximately 8-9 ml of W5 is added to the protoplast, followed by centrifugation at 75×g for 5 minutes.

Then, the density of the protoplast suspensions is determined with a hemocytometer. The protoplasts of both suspensions protoplasts are brought together with a density of $9 \times 10^5$ protoplasts/ml for fusion in a petri dish as drops using a micro pipette and left to rest in the dark for 15 minutes to enable the protoplasts to adhere to the bottom of the petri dishes. Then approximately 60 μl of PEG1-solution (PEG4000 400 g/l, $CaCl_2 \cdot 2H_2O$ 7.35 g/l, glucose 54.5 g/l) is added to each drop of protoplasts followed after 3-5 minutes by addition of 4 to 9 ml PEG2 (PEG4000 133 g/l, $CaCl_2 \cdot 2H_2O$ 9.85 g/l, sorbitol 12.21 g/l, glucose 18.02 g/l) solution. After 3-5 minutes the solution is removed and 4 to 9 ml of PEG3 (PEG4000 67 g/l, $CaCl_2 \cdot 2H_2O$ 12.2 g/l, sorbitol 15.12 g/l, glucose 9.01 g/l) is added. After 3-5 minutes the solution is removed and 4 to 9 ml of B-medium (according to Pelletier et al., 1983) is added and repeated after 3-5 min for a second time. Finally, the petri dishes are sealed and stored in the dark.

Subsequently, the fusion products being a B. rapa with the nucleus of B. rapa var. cymose, Ogura mitochondria, and B. rapa chloroplasts were grown as described in Pelletier et al. (1983). The fusion products were crossed with a B. rapa line (Cime di Rapa) as BC1. When the BC1 plants were sown and a marker analysis was performed on the three organelles—mitochondria, nucleus and chloroplasts, 100% of the plants confirmed to carry the correct and predicted organelle composition (i.e. nucleus of B. rapa, Ogura mitochondria, and B. rapa chloroplasts). Furthermore, the plants were crossed with a B. rapa nipposinica var. japonica, a parachinensis and a pekinensis type. After 4-5 weeks, seeds were collected and sown for another backcross generation and were also confirmed to carry the correct and predicted organelle composition.

Identification of Chlorosis Resistant B. rapa

A marker analysis was performed on the three organelles—mitochondria, nucleus and chloroplast to confirm that the B. rapa plants comprised 100% of the correct and predicted organelle composition (i.e. B. rapa chloroplasts, nucleus of B. rapa and mitochondria of Ogura). Markers in Table 1 below can be used to confirm that the mitochondria are of Ogura (R. sativus), and that the nucleus and chloroplast are of B. rapa, i.e. and to exclude that the mitochondria are comprised of other sequences not originating from Ogura or to exclude that the chloroplasts are from Brassica sources other than B. rapa, such as chloroplasts that may originate from B. oleracea.

TABLE 1

| Marker sequences organelles Brassica plants | |
|---|---|
| | Sequence |
| Chloroplast marker | |
| Cp Rapa 1 (SEQ ID No. 1) | GAAATATGACCAACTGTGGTTCGAATATATATAA AAAAAGTTTGTTTTTTTACACTTCTTACTATCAGAT AGTGTGCAT |
| Cp Oleracea 1 (SEQ ID No. 2) | GAAATATGACCAACTGTGGTTCGAATATATATAC AAAAAGTTTGTTTTTTTACACTTCTTACTATCAGAT AGTGTGCAT |
| Cp Rapa 2 (SEQ ID No. 3) | CTCGAACAAGTAATCGAAAAGATTCTGGAGCATC TTCTGGTTTAGGTATTGCTCCTCCAATGATAGTGG TACCAAGTACTTCTTGGCGAGCTCTAATATGA |
| Cp Oleracea 2 (SEQ ID No. 4) | CTCGAACAAGTAATCGAAAAGATTCTGGAGCATC TTCTGGTTTAGGTATTGTTCCTCCAATGATAGTGG TACCAAGTACTTCTTGGCGAGCTCTAATATGA |
| Cp Rapa 3 (SEQ ID No. 5) | AAGGATTCATAAGTAGTTGTTAACGGAGTTGAAG TTACCAAATTCTGAGGAGTCGGTATCAATTTATGC CTAATTGCTCCGCCTATAGTTCCCTTAACTACATTT TCTAAACGAGCC |
| Cp Oleracea 3 (SEQ ID No. 6) | AAGGATTCATAAGTAGTTGTTAACGGAGTTGAAG TTACCAAATTCTGAGGAGTAGGTATCAATTTATGC CTAATTGCTCCGCCTATAGTTCCCTTAACTACATTT TCTAAACGAGCC |

TABLE 1-continued

| Marker sequences organelles *Brassica* plants | |
| --- | --- |
| | Sequence |
| Nucleus marker | |
| N *Rapa* 1 (SEQ ID No. 7) | TCGGTCAAGGACTCGGATACATCGATGCTGGAGC ACAAAAGAAGCAGAAGGAAGAGAAAACAGCGA TGGAGGAAGAGATGGAGAAGCTGAGAAGAGATC AGGCGGA |
| N *Oleracea* 1 (SEQ ID No. 8) | TCGGTCAAGGACTCGGATACATCGATGCTGGAGC ATAAGAAGCAGAAGGAAGAGAAAACAGCGA TGGAGGAAGAGATGGAGAAGCTGAGAAGAGATC AGGCGGA |
| N *Rapa* 2 (SEQ ID No. 9) | CTGTGCCTCGGAAAGGTGAGTATCTTGTGTTGGAA GTTTATTTTCTTTGTCTCTCAGTGATCTCATGCATA CACAAACTTTTGTGCAGCCTGCGGATATATACCTG ATTGATGAGCCAAGTG |
| N *Oleracea* 2 (SEQ ID No. 10) | CTGTGCCTCGGAAAGGTGAGTATCTTGTGTTGGAA GTTTGTTTTCTTTGTCTCTCAGTGATCTCATGCATA CACAAACTTTTGTGCAGCCTGCGGATATATACCTG ATTGATGAGCCAAGTG |
| Mitochondria marker | |
| Mt *Ogura* (SEQ ID No. 11) | AAGAAGCAAAATCTCATTCAATTTGAAATAGAAG AGATCTCTATGCCCCCTGTTCTTG |
| Mt *Rapa* 1 Fw (SEQ ID No. 12) | TCCCCTCTGTCCCTATGTTG |
| Mt *Rapa* 1 Rev (SEQ ID No. 13) | GAGGTGTTGCCTATCCAGGT |
| Mt *Rapa* 2 Fw (SEQ ID No. 14) | TTCGTTCGTTCACTTCGTTCT |
| Mt *Rapa* 2 Rev (SEQ ID No. 15) | AGGCCTTTCCTTAAGCTTCCT |
| Mt *Rapa* 3 Fw (SEQ ID No. 16) | GGAAGGATCGAACCATAGGAA |
| Mt *Rapa* 3 Rev (SEQ ID No. 17) | TTGATGAGCCTTTACGAGTTGA |
| Mt *Oleracea* 1 Fw (SEQ ID No. 18) | CGAAAACCTTCTGTTCTGTGG |
| Mt *Oleracea* 1 Rev (SEQ ID No. 19) | CGGAGCGTAACCACTTTCTT |
| Mt *Oleracea* 2 Fw (SEQ ID No. 20) | ATTCCCCACCCAACCAATAC |
| Mt *Oleracea* 2 Rev (SEQ ID No. 21) | AAGAGCAGCTTTCTCCGTTCT |
| Mt *Oleracea* 3 Fw (SEQ ID No. 22) | TTGCTGTATCGGAAAGTCCA |
| Mt *Oleracea* 3 Rev (SEQ ID No. 23) | GCATGTCGTAAGCGAGTCAA |

For example, the SNP marker SEQ ID No. 1 and SEQ ID No. 2 are used for the identification of the origin of the chloroplast being from *B. oleracea* or *B. rapa*. Chloroplasts that originate from the *B. oleracea* will have a "C" at position 34bp in SEQ ID No. 2, whereas chloroplasts that originate from *B. rapa* will have an "A" at position 34bp. The SNP marker SEQ ID No. 7 and SEQ ID No.8 are used for the identification of the origin of the genomic DNA being from *B. oleracea* or *B. rapa*. When the genomic DNA originates from *B. oleracea* there will be a "T" at position 36bp and a "G" at position 39bp in SEQ ID No. 8, whereas if the genomic DNA originates from the *B. rapa* there will be a "C" at position 36bp and an "A" at position 39bp. SEQ ID No. 11 was used for the identification of the origin of the mitochondria being from Ogura to confirm the CMS *B. rapa*.

In addition, SEQ ID No. 12 to 23 are primer sequences to determine if the mitochondria comprise *B. rapa* or *B. oleracea* mitochondrial sequences. PCR reaction was performed on plant total genomic DNA to discriminate between *B. rapa* and *R. sativus* mitochondrial genome as well as between *B. oleracea* and *R. sativus* mitochondrial genome. Following PCR, the product was incubated with restriction enzyme, according to table 2 and scored for their expected fragment sizes to determine the mitochondrial genome origin. The product after digestion was put on a 2% agarose gel and fragment sizes were analysed. For example, following PCR with SEQ ID No. 14 and 15 and digestion with DdeI, the *R. sativum* specific mitochondrion DNA product contains 4 fragments of 357, 81, 63 and 57 base pairs in size, whereas the *B. rapa* specific mitochondrion DNA product contains 5 fragments of 285, 81, 75, 63 and 57 base pairs in size.

TABLE 2

| Mitochondrial genome analysis Brassica | | | | | |
|---|---|---|---|---|---|
| Primer combination | Product size | Restriction | Products after restriction (nt) per mitochondria | | |
| (SEQ ID No.) | (nt) | Enzyme | B. rapa | B. oleracea | R. sativus |
| 12 + 13 | 1417 | Hpy188I | 687 + 397 + 281 + 39 + 17 | — | 571 + 397 + 281 + 117 + 39 + 17 |
| 14 + 15 | 549 | DdeI | 285 + 81 + 75 + 63 + 57 | — | 357 + 81 + 63 + 57 |
| 16 + 17 | 673 | HaeIII | 377 + 164 + 82 + 50 | — | 377 + 246 + 50 |
| 18 + 19 | 420 | Bsp119I | — | 420 | 341 + 40 + 40 |
| 20 + 21 | 773 | ApoI | — | 773 | 474 + 303 |
| 22 + 23 | 568 | SacI | — | 317 + 182 + 77 | 317 + 255 |

Four plants have been included for marker analysis; *B. rapa* (wild type), *B. oleracea* (wild type), *B. rapa* "old" CMS (chlorotic), *B. rapa* "new" CMS (non-chlorotic, plant of present invention). Table 3 provides an overview, wherein "+" indicated that the marker was present and a "−" indicated that the markers were absent in the plants. In respect to the PCR markers (SEQ ID No. 12 to 23) on the basis of the product fragments the plants were scored R (*rapa*) or O (*oleracea*), indicating the origin of the mitochondrial genome, and the "−" indicated that the PCR did not yield a PCR product, i.e. an absence of *B. rapa* or *B. oleracea* mitochondrial sequences.

rosis was evaluated prior to flowering in a cold greenhouse was done by eye. After four weeks of seedlings of *B. rapa* growing in a glass house were transferred to a non heated glass house for winter cultivation (at temperatures of between 5 to 12° C.).

Chlorosis was scored by visual inspection of the colour of the plant tissues, which gradually turn from green into yellow as the result of from partial failure to develop chlorophyll. A reduction of chlorophyll leads to yellowing of the tissue. Wild type *B. rapa* plants that are unaffected (i.e. not affected by a pathogen or nutrient deficiency which causes chlorophyll degradation) are have a normal green

TABLE 3

| Marker analysis on organelles of Brassica plants. | | | | | | | | | | | | | | | | |
|---|---|---|---|---|---|---|---|---|---|---|---|---|---|---|---|---|
| | Chloroplast | | | | | Nucleus | | | | | Mitochondria | | | | | |
| Seq ID No. | 1 | 2 | 3 | 4 | 5 | 6 | 7 | 8 | 9 | 10 | 11 | 12 + 13 | 14 + 15 | 16 + 17 | 18 + 19 | 20 + 21 | 22 + 23 |
| *B. rapa* | + | − | + | − | + | − | + | − | + | − | − | R | R | R | − | − | − |
| *B. oleracea* | − | + | − | + | − | + | − | + | − | + | − | − | − | − | O | O | O |
| *B. rapa* "old" CMS | − | + | − | + | − | + | + | − | + | − | + | − | − | − | − | − | − |
| *B. rapa* "new" CMS | + | − | + | − | + | − | + | − | + | − | + | − | − | − | − | − | − |

Results show that plants of present invention (*B. rapa* "new" CMS) only comprise chloroplasts and a nucleus that originate from *B. rapa*, wherein the chloroplasts are 100% associated with markers for *B. rapa* chloroplasts, and the nucleus is associated with markers for *B. rapa* nucleus. The chlorosis resistant CMS *B. rapa* plant of present invention was also tested to comprise only a mitochondrial genome of the Ogura type associated with SEQ ID No. 11, i.e. being a sterile (CMS) plant. No mitochondria genome of *B. rapa* or *B. oleracea* was present in the plant of present invention as indicated with the markers SEQ ID No 12 to 23.

Evaluation of Chlorosis in *B. rapa*

To evaluate yellowing in the developed plant materials, CMS *B. rapa* plant according to present invention ("new"), a CMS *B. rapa* plant known in the art ("old") and a wild type *B. rapa* plant have been tested for chlorosis under cold conditions. At the same time, the flower quality, plant growth and stability of sterility have been evaluated. Chlophenotype, where no chlorosis was observed and where the plant develops regular, green plant tissue. These plants obtain a score of 5 and are used as the benchmark in a scoring scale ranging from 1 to 5. A score of 1 refers to plants that show severe chlorosis with upper leaves markedly yellow and lower leaves very chlorotic. A score of 2 refers to very chlorotic with pronounced interveinal yellowing. A score of 3 refers to mild to moderate chlorosis, interveinal yellowing on the leaves. A score of 4 refers to near normal (wild type) phenotype, light green/interveinal yellowing, no chlorotic leaves. And a score of 5 thus refers to a green non yellowing phenotype of the *B. rapa* plant. *B. rapa* plants that obtain a score of 1 to 4, thus show chlorosis and these plants are not acceptable for commercial sale.

After 3-4 weeks and until commercial maturity in the non heated glass house (at temperatures between 5-12° C.), chlorotic symptoms were visible on the "old" CMS *B. rapa* plants (plant not according to present invention), scoring a 3 on the chlorosis as defined above. No chlorisos was observed on the "new" CMS *B. rapa* plants of present invention, which were scored a 5 on the chlorosis and was comparable to the wild type *B. rapa* plant. FIGS. 1 and 2 show plants and leaves of a CMS *B. rapa* plant according to present invention ("new") having a *B. rapa* nucleus, Ogura mitochondria and *B. rapa* chloroplast that is chlorosis resistant, a wild type *B. rapa* plant, and a prior art CMS *B. rapa* plant ("old") having a *B. rapa* nucleus, Ogura mitochondria and *B. oleracea* chloroplast. Chlorosis is especially visible as interveinal yellowing on upper trifoliates and on the stem of the leaves, gradually moving towards the leave on the "old" *B. rapa* plants. No chlorosis was visible on the CMS *B. rapa* plant of present invention during these 3 to 4 weeks under identical conditions. All plants in the three *B. rapa* groups were similar in size and shape, showing no adverse affects of the on plant growth and development. Also after further backcrosses in F1 no chlorosis and adverse effects on plant growth and plant development was observed in the CMS *B. rapa* plants of present invention.

Furthermore, the flower quality was assessed and plant sterility was conformed at the initial flowering stage. In the *B. rapa* plant of present invention, no pollen development and no self-pollination occurrence was observed. This assessment was followed twice a week in order to control newly opened flowers over the different stages of flowering until all flowers were opened. In addition, controlled normal development of petals, stigmas and nectar was observed, apart from the expected abnormal pollen anthers carrying no pollen in comparison with a wild type *B. rapa* plants (Cima di *Rapa*), see FIG. 3. FIG. 3 shows the flowers of a chlorosis resistant CMS *B. rapa* plant of present invention (upper picture) and a wild type male fertile *B. rapa* plant (lower picture). Pollen are clearly visible on the wild type plant having fully developed anthers that carry pollen grains, whereas the CMS *B. rapa* plant of present invention shows undeveloped anthers and the anthers are carrying no pollen at all.

Confirmation of female fertility of the *B. rapa* plant of present invention was performed by artificial hand pollination of sterile flowers with a wild type *B. rapa* pollen collected from neighbouring plant in the same greenhouse. Seed setting, ripening and drying were controlled during the season every week from pollination to harvest.

The invention claimed is:

1. A method of producing a chlorosis resistant CMS *Brassica rapa* plant, comprising the steps of:

a) protoplast fusion of protoplasts of a fertile *Brassica rapa* plant with protoplasts of a CMS *Brassica rapa* plant as a CMS cytoplasm donor, wherein the cytoplasm donor comprises chloroplasts of a diploid *Brassica oleracea* plant and *Raphanus sativus* mitochondria, wherein mitochondria of the CMS cytoplasm donor are combined with chloroplasts and nucleus of the fertile *Brassica rapa* plant; and b) selecting a protoplast fusion product, wherein:

i. at least 95% of fusion product chloroplasts are *Brassica rapa* chloroplasts comprising one or more sequences selected from the group consisting of SEQ ID NO: 1, SEQ ID NO: 3 and SEQ ID NO: 5;

ii. the fusion product nuclear genome is a *Brassica rapa* nuclear genome comprising SEQ ID NO: 7 and/or SEQ ID NO: 9;

iii. the fusion product does not comprise *Brassica oleracea* chloroplasts that comprise one or more sequences selected from the group consisting of SEQ ID NO: 2, SEQ ID NO: 4, and SEQ ID NO: 6; and iv. the fusion product comprises a mitochondrial genome of *Raphanus sativus* comprising the sequence of SEQ ID NO: 11.

2. The method of claim 1, further comprising:

c) crossing the selected fusion product with a wild-type *Brassica rapa* plant to produce progeny, and selecting from the progeny a CMS *Brassica rapa* plant that is chlorosis resistant.

3. The method of claim 1, wherein the CMS *Brassica rapa* plant is selected from the group of *Brassica rapa* subspecies consisting of: *Rapa, Pekinensis, Glabra, Chinensis, Rapifera, Oleifera, Parachinensis, Perviridis, Brassica Narinosa, Trilocularis*, and *Mizuna*.

4. The method of claim 1, wherein the *Brassica rapa* subspecies is *Rapa* or Pekinensis.

5. The method of claim 1, wherein the chlorosis resistant CMS *Brassica rapa* plant is obtainable by growing seeds deposited under NCIMB Accession Number 43622.

* * * * *